United States Patent
Silberer et al.

(10) Patent No.: US 11,798,401 B2
(45) Date of Patent: Oct. 24, 2023

(54) METHOD FOR WIRELESS TRANSMISSION OF DATA IN A MEDICAL OR DENTAL SYSTEM AND SUCH A MEDICAL OR DENTAL SYSTEM

(71) Applicant: W&H Dentalwerk Bürmoos GmbH, Bürmoos (AT)

(72) Inventors: Bernhard Silberer, Michaelbeuern (AT); Michael Reiter, Elsbethen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 319 days.

(21) Appl. No.: 17/189,023

(22) Filed: Mar. 1, 2021

(65) Prior Publication Data
US 2021/0280053 A1 Sep. 9, 2021

(30) Foreign Application Priority Data
Mar. 3, 2020 (EP) .................................... 20160636

(51) Int. Cl.
G08C 17/02 (2006.01)
A61B 17/00 (2006.01)
A61C 1/00 (2006.01)

(52) U.S. Cl.
CPC .............. *G08C 17/02* (2013.01); *A61B 17/00* (2013.01); *A61C 1/0023* (2013.01);
(Continued)

(58) Field of Classification Search
CPC .... G08C 17/02; G08C 2201/70; A61B 17/00; A61B 2017/00212; A61B 2017/00221;
(Continued)

(56) References Cited

U.S. PATENT DOCUMENTS

2008/0080403 A1* 4/2008 Guo ........................ H04L 5/003
370/271
2011/0275327 A1* 11/2011 Lint ...................... A61C 1/0023
455/66.1
(Continued)

FOREIGN PATENT DOCUMENTS

| JP | 2006-068396 A | 3/2006 |
| JP | 2012-105073 A | 5/2012 |
| WO | 2004/030563 A1 | 1/2006 |

OTHER PUBLICATIONS

Anonymous: "Quality of service—Wikipedia," https://en.wikipedia.org/w/index.php?title=Quality_of_service&oldid=883636447 (Feb. 16, 2019).
(Continued)

*Primary Examiner* — Lester G Kincaid
*Assistant Examiner* — Maryam Soltanzadeh
(74) *Attorney, Agent, or Firm* — Wood, Phillips, Katz, Clark & Mortimer

(57) ABSTRACT

A method for wireless transmission of data in a medical or dental system which has a foot control and at least two devices which can selectively be controlled wirelessly by the foot control, each device being assigned a specific identification code, wherein a controller provided in the foot control selects on the basis of data packets the device to which operating data are wirelessly transmitted, wherein each of the devices has its own data packet which comprises the specific identification code of the device and an individual rank assigned to this device of a ranking of the devices.

20 Claims, 2 Drawing Sheets

(52) U.S. Cl.
CPC ............ *A61B 2017/00212* (2013.01); *A61B 2017/00221* (2013.01); *A61B 2017/00973* (2013.01); *G08C 2201/70* (2013.01)

(58) Field of Classification Search
CPC ........ A61B 2017/00973; A61C 1/0023; G05G 1/305; G16H 40/40; H04L 67/12
See application file for complete search history.

(56) References Cited

U.S. PATENT DOCUMENTS

| | | | |
|---|---|---|---|
| 2016/0105904 A1* | 4/2016 | Fischer | ................ H04W 4/023 455/39 |
| 2019/0201136 A1 | 7/2019 | Shelton, IV et al. | |
| 2019/0205001 A1 | 7/2019 | Messerly et al. | |

OTHER PUBLICATIONS

Anonymous: :Traffic shaping—Wikipedia, https://en.wikipedia.org/w/index.php?title=Traffic_shaping&oldid=725195597 (Jun. 14, 2016).).

Search Report for European Application No. 20160636.5, dated Sep. 4, 2020.

* cited by examiner

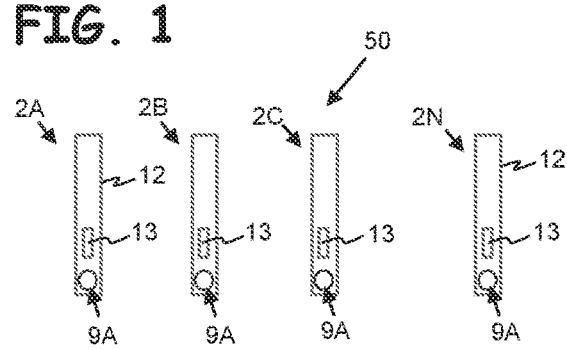
FIG. 1
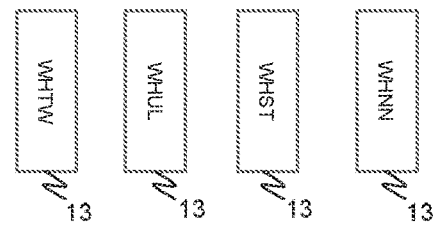
FIG. 2
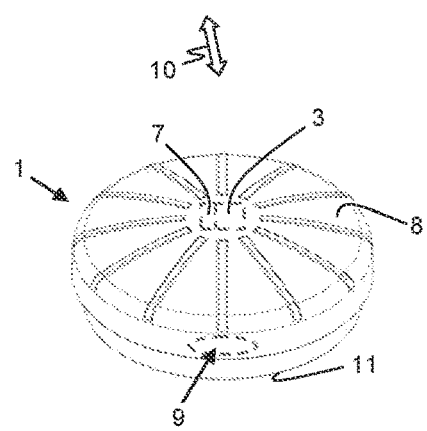
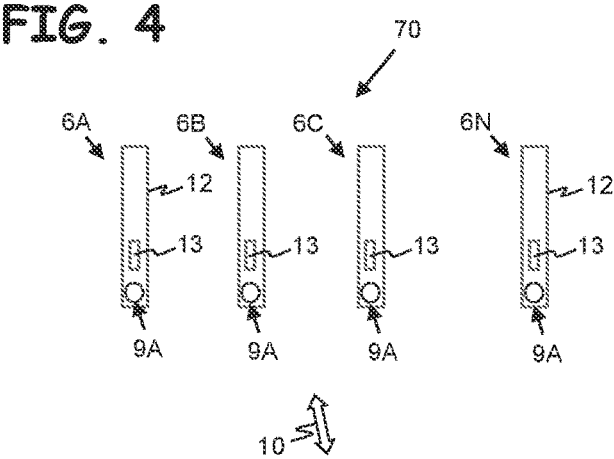
FIG. 3
FIG. 4
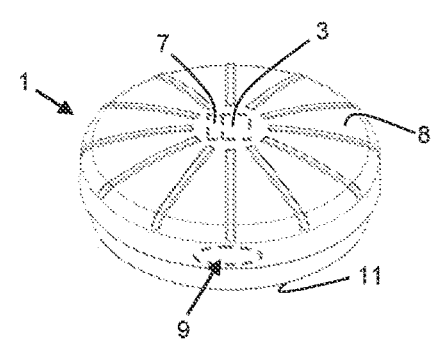
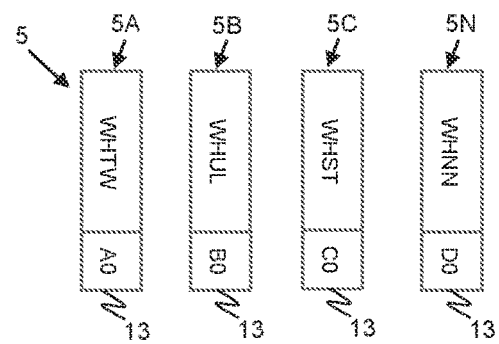
FIG. 5

METHOD FOR WIRELESS TRANSMISSION OF DATA IN A MEDICAL OR DENTAL SYSTEM AND SUCH A MEDICAL OR DENTAL SYSTEM

CROSS REFERENCE TO RELATED APPLICATION

The present application claims priority from pending European Patent Application No. 20160636.5, filed Mar. 3, 2020, which is incorporated herein by reference.

FIELD

The present invention relates to a method for wireless transmission of data in a medical or dental system and to such a medical or dental system having a foot control and a plurality of medical or dental devices for treatment and/or diagnosis, wherein at least two of the plurality of devices can be selectively controlled by the foot control.

DESCRIPTION OF PRIOR ART

Patent application US 2005/0251228 A1 discloses a foot control configured to selectively wirelessly control one of a plurality of medical devices. The user selects the device to which data is to be transmitted wirelessly by the foot control through a control element on the foot control. Such a selection of the device via an actuator at the foot control is impractical for the user, possibly cumbersome due to the footwear, and thus includes many possibilities for error.

SUMMARY

It is therefore an object to create methods and corresponding devices or systems in which the selection of the device to which data are to be wirelessly transmitted from the foot control is easier for the user and the possibilities of incorrect operation are reduced.

For carrying out the method according to the invention, a medical or dental system is provided which comprises a foot control and a plurality of medical or dental devices for treatment and/or diagnosis, for example a handpiece or a table top device with a handpiece. At least two of the plurality of devices are selectively controllable wirelessly by the foot control, wherein each device controllable by the foot control is assigned a specific identification code, that is, in particular, an individual and/or unique and/or unchangeable identification code. The method according to the invention for wireless transmission of data in the medical or dental system is defined in that a controller (control logic) provided in the foot control selects, on the basis of data packets, that device controllable by the foot control to which operating data, in particular control data for treatment and/or diagnosis, are transmitted wirelessly, wherein each device controllable by the foot control being assigned its own data packet. Each of these data packets comprises (1) the specific identification code of the device controllable by the foot control to which the data packet is assigned, and (2) an individual rank assigned to this device (to which the data packet is assigned) in a ranking of the foot-controllable devices. Thus, a data packet is associated with a device controllable by the foot control and comprises only its specific identification code and its unique, individual rank. A specific identification code and a unique, individual rank thus preferably form an inseparable unit in the form of the data packet that is assigned to a specific device.

As described in detail below, the controller provided in the foot control thus preferably selects on the basis of a predetermined ranking, according to which each device controllable by the foot control is assigned a predetermined, individual rank comprised in the respective data packet, that device to which (currently or in the following) operating data or control data for treatment and/or diagnosis are to be transmitted wirelessly.

Thus, the selection via the foot control of the device to be controlled, which is cumbersome and error-prone for the user, is advantageously omitted.

The wireless transmission of data comprises in particular radio transmission in the frequency range of radio waves, for example by Bluetooth or WLAN. Data transmission with wavelengths in the infrared range is also conceivable.

The specific identification code assigned to each device controllable by the foot control, for example a handpiece, comprises, for example, a numeric or alphanumeric string, a PIN code, a device address or a MAC address. Preferably, each of the devices controllable by the foot control comprises a memory element in which the respective specific identification code associated with the device is stored. This memory element and/or the identification code preferably cannot be overwritten and/or deleted by the user. Thus, in an advantageous manner, an unambiguous identification or assignment of the device is possible, in particular by the foot control or controller which receives the identification code or is configured to receive it.

Preferably, the devices controllable by the foot control are configured to send their respective specific identification code or their respective data packet wirelessly to the common foot control, which is configured to control the device. In particular, if the foot control receives a specific identification code, preferably as part of the data packet, it is thus recognizable for the foot control whether a (particular) device controllable by the foot control or which device controllable by the foot control is (currently) active, for example is switched on or is in an operating or activity mode or in operation, and/or whether a (particular) device controllable by the foot control or which device controllable by the foot control is (currently) ready for communication or data transmission with the foot control. Correspondingly, if the foot control does not receive a specific identification code or a specific data packet, it is thus advantageously recognizable for the foot control that a specific device controllable by the foot control or which device controllable by the foot control is (currently) is not active, for example is not switched on or is not in an operating or activity mode or in operation, and/or that a specific device controllable by the foot control or which device controllable by the foot control is (currently) is not ready for communication or data transmission with the foot control.

The controller provided in the foot control, which is configured to receive the identification codes or the data packets, comprises in particular electronic circuits and/or software. Preferably, the controller is configured to process received identification codes or data packets and/or to compare them with identification codes or data packets (of the devices controllable by the foot control) stored in the foot control and/or to evaluate them in order to select the device to which operating data or control data for treatment and/or diagnosis are transmitted wirelessly. This offers the applicant a very user-friendly possibility to determine the device to be controlled by the foot control.

The selection by the controller of the device to which operating data or control data for treatment and/or diagnosis (currently) are to be transmitted wirelessly is based on a (predetermined) ranking of the devices controllable by the foot control. Preferably, the ranking comprises an order of precedence that is distinguishable, in particular, in a simple manner for or with the aid of the controller. In the ranking, an individual and/or unique and/or own and/or predetermined rank is assigned to each device controllable by the foot control, wherein each rank occurs only once in the ranking and thus, in particular, each data packet comprises its own, distinct or unique rank. The ranks preferably have different numerical values, for example a rank with the value 1, a further rank with the value 2, a further rank with the value 3 etc. is provided. Of course, ranks with other values are also possible, for example with strings of different lengths. The ranking can, for example, be in the form of a list. This advantageously provides a means of selecting the device to be controlled which is extremely easy to implement in terms of both hardware and software.

According to a preferred embodiment, the data packets of the devices controllable by the foot control are provided, in particular stored, in the foot control. Thus, the data packets are stored centrally in an advantageous manner and can be easily adapted or supplemented, for example. The data packets are stored in particular in a memory element of the foot control, the memory element preferably being communicatively connected to the controller or being configured as part of the memory logic. Preferably, the foot control stores at least two specific data packets of two devices and correspondingly two individual ranks, for example an identification code AAA of a first device to which a rank 1 is assigned and an identification code BBB of a second device to which a rank 2 is assigned. Of course, there may be further data packets with specific individual identification codes for additional devices, for example CCC, DDD, EEE, . . . and further ranks 3, 4, 5, . . . each assigned to one of the devices.

Preferably, one or more of the devices controllable by the foot control transmit (at a given time) their respective specific identification code stored in the device to the foot control, wherein the foot control receives, preferably stores or caches this specific identification code(s), and the controller recognizes, on the basis of the received identification code(s) and the data packets (stored in the foot control), which of the devices controllable by the foot control is/are active and which individual rank the active device(s) occupies(s) in the ranking order. Particularly preferably, the controller compares each identification code sent by a device and received with the identification codes provided in the data packets and recognizes from this which of the plurality of devices controllable by the foot control is (currently) active, for example is switched on or is in an operating or activity mode or is in operation, and is thus basically ready for communication or data transmission with the foot control.

By comparing the transmitted and received identification code with the identification codes provided in the data packets, the controller can also determine the individual rank of each active device, since, according to the ranking, an individual rank is assigned to each device controllable by the foot control, i.e., an individual rank is assigned to the identification code of the device. This advantageously provides a very reliable method for determining the active devices and in particular their respective individual ranks.

Preferably, the method is configured such that if the foot control receives (at a certain point in time or within a limited period of time) specific identification codes from two or more devices controllable by the foot control, then the foot control selects—in particular based on the comparison of the transmitted and received identification code with the identification codes provided in the data packets and the ranks of the active devices determined therefrom—that device for wireless transmission of operating data or control data for treatment and/or diagnosis, from which the foot control has received an identification code and which is a prioritized individual rank or value in the ranking compared to the other devices from which the foot control has received an identification code. The prioritized rank may have, for example, a preferred or superior or higher or lower position in the ranking order or in a ranking list or a preferred or superior or higher or lower value compared to the other individual ranks of the active devices. Advantageously, this provides a simple and reliable approach for wireless transmission of operational data.

According to the simplest embodiment, the medical or dental system comprises exactly two devices that are controllable by the foot control. These two devices are each assigned a specific identification code, for example WHTW and WHUL, which are stored in respective memory elements of the devices. If both devices are active and both devices transmit their respective, specific identification code simultaneously (at a certain point in time or during a limited period of time) and the (common) foot control receives both identification codes, the foot control compares the two received identification codes with the identification codes of the stored data packets and thus also determines the respective individual rank assigned to the respective identification code in the ranking. For example, the identification code WHTW is assigned the individual rank 0 and the identification code WHUL is assigned the individual rank 1. For example, if the controller is configured such that the lowest individual rank or value in the ranking is prioritized, the foot control establishes a wireless communication link for transmitting operational data or control data for treatment and/or diagnostics only to the device with identification code WHTW (with individual rank 0). According to this embodiment, the foot control thus does not establish a wireless communication link for transmitting operational data to the device with identification code WHUL (with individual rank 1).

Accordingly, the embodiment described in the foregoing applies to medical or dental systems having more than two devices controllable by the foot control, and in which (at a given time or during a limited period of time) more than two devices transmit their respective identification codes simultaneously. Again, the controller receives and compares the more than two specific identification codes of the more than two active devices with the identification codes of the data packets and thus also determines the respective individual ranks of the more than two active devices. Based on the determined individual ranks, the foot control establishes a wireless communication link for transmitting operational data or control data for treatment and/or diagnosis only to that device whose individual rank is prioritized.

According to an alternative embodiment, each device controllable by the foot control has its associated data packet. The data packets of the devices controllable by the foot control are thus preferably provided, in particular stored, in the respective device whose specific identification code and unique, individual rank it comprises. Each data packet can be (wirelessly) transmitted individually from 'its' device to the foot control. Thus, in an advantageous way, additional devices can be added to the method and system very easily, in particular without any adjustments or additions to the foot control. The respective data packet is preferably stored in a memory element of the respective device.

Preferably, the method is configured such that if the foot control receives data packets from two or more devices controllable by the foot control, then the foot control selects that device for wireless transmission of operational data, in particular control data for treatment and/or diagnosis, from which the foot control has received a data packet and whose individual rank is a prioritized rank or value compared to the other devices from which the foot control has received a data packet. The prioritized individual rank may have, for example, a preferred or superior or higher or lower position in the ranking or in a ranking list or a preferred or superior or higher or lower value compared to the other individual ranks of the active devices.

Particularly preferably, the foot control stores or caches the received data packets of the two or more devices controllable by the foot control, in particular in a memory element of the foot control. The controller of the foot control accesses these received and stored data packets and in particular compares the individual ranks of the received and stored data packets. Based on this comparison, the controller selects the identification code, i.e., the device with the prioritized rank, to which the foot control establishes wireless communication for transmitting operational data.

According to the simplest embodiment, the medical or dental system comprises exactly two devices that are controllable by the foot control. A data packet with a specific identification code and an individual rank is assigned to each of these two devices and is stored in particular in a memory element of the respective device. For example, a data packet of one device comprises the identification code WHTW and the rank 10, the data packet of the other device comprises, for example, the identification code WHUL and the rank 5. If both devices are active and both devices send (at a specific time or during a limited period of time) their respective data packet simultaneously and the (common) foot control receives both data packets, the controller compares the individual ranks of the two devices comprises in the respective data packets. For example, if the controller is such that the higher individual rank or value of the ranking is prioritized, the foot control establishes a wireless communication link for transmitting operational data or control data for treatment and/or diagnostics only to the device with the identification code WHTW (with the individual rank 10). According to this embodiment, the foot control thus does not establish a wireless communication link for transmitting operational data to the device with the identification code WHUL (with the individual rank 5).

The embodiment described in the foregoing applies accordingly to medical or dental systems with more than two devices that are controllable with the foot control, and where (at a given time or during a limited period of time) more than two devices send their respective data packet simultaneously. Again, the controller compares the individual ranks of the received data packets. Based on this comparison, the foot control establishes a wireless communication link for transmitting operational data or control data for treatment and/or diagnosis only to that device whose individual rank is prioritized.

Preferably, if the foot control receives (at a given time or during a limited period of time) a specific identification code or data packet from only one device controllable by the foot control, then the controller of the foot control selects this device for wireless transmission of operational data or control data for treatment and/or diagnosis. This advantageously ensures that the method can be performed even if only one of the plurality of devices controllable by the foot control is active or switched on. In particular, the controller is configured not to perform a determination or comparison of the individual ranks when only one specific identification code or data packet is received.

Preferably, in the method for wireless transmission of data, it is provided that data packets, in particular the individual ranks of the devices controllable by the foot control, are unchangeable for the user. The user can thus in particular not change the rank of a device, for example its value or position in a ranking or ranking list. For example, the individual ranks of the devices are determined and stored during the manufacture of the devices or the foot control. This advantageously prevents incorrect operation by the user.

Alternatively, in the method for wireless transmission of data, it is provided that the individual ranks of the devices controllable by the foot control are changeable for the user. The user can thus in particular change or select the rank of a device, for example its value in a data packet or its value or position of a ranking or ranking list. Advantageously, this allows the user greater individual freedom in said method for wireless transmission of data and in the operation of the medical or dental system.

Preferably, the individual ranks of the data packets and/or of the ranking are determined by pairing and/or during pairing (i.e., the initial bringing into communicative connection) of the devices controllable by the foot control with the foot control. Since the medical or dental system has multiple devices selectively and wirelessly communicating with and controllable by a common foot control, it is necessary to pair each of the devices with the foot control prior to initial control of the devices by the foot control. By determining the individual ranks by pairing and/or during pairing, a very simple possibility is created for the user to determine the individual ranks or ranking of the devices, in particular according to his own wishes. In particular, no additional time is required for determining the individual ranks in an advantageous manner.

Preferably, it is provided that the individual ranks are determined by the order in which the devices controllable by the foot control are paired with the foot control. For example, that device which is first paired with the foot control receives the highest or lowest rank or value or rank or value 1, the device which is next paired with the foot control receives the next highest or lowest rank or value or rank or value 2, the device which is subsequently paired with the foot control receives the next highest or lowest rank or value or rank or value 3, etc.

Alternatively or additionally, it is provided that the individual ranks are determined by drivers used for pairing and/or the type of pairing between the foot control and the devices controllable by the foot control. For example, a driver for wired pairing and a driver for wireless pairing are provided. For example, the type of pairing comprises a wired connection and a wireless connection. For example, that device which is paired wirelessly with the foot control or in which a driver for wireless pairing is used is given a rank or value of 1 and a device which is paired through a wire with the foot control or in which a driver for wired pairing is used is given a rank or value of 2.

The two ways of determining individual ranks described in the foregoing are effected by pairing and during pairing. Alternatively or additionally, it may be provided that the individual ranks are determined during pairing between the foot control and the devices controllable by the foot control by a selection made by the user of the medical or dental system. For example, the user selects the individual rank of the device being paired with the foot control via an actuator or control panel on the foot control or on the device.

The individual ranks determined by the pairing and/or during the pairing are preferably stored in the memory element of the device and/or foot control during or after completion of the pairing, in particular together with or in addition to the identification code of the respective device, in order to form the data packets in particular.

Preferably, in the method for wireless transmission of data, it is provided that the foot control is shifted from a mode with at least reduced transmission power to an operating mode with increased transmission power compared to the at least reduced transmission power by receiving an identification code or data packet of a device. Advantageously, this puts the foot control into the operating mode without the user having to actively actuate the foot control. Alternatively, the user actuates a user interface or actuating element of the foot control to put it into the operating mode.

Preferably, in the method for wireless transmission of data, it is provided that after the selection by the foot control for transmission of the operating data, in particular the control data, and/or during the transmission of the operating data, the device sends at least its specific identification code or its data packet to the foot control, in particular repeatedly and/or within predetermined time intervals, in order to maintain the wireless communication between the foot control and the device.

Preferably, in the method for wireless transmission of data, it is provided that prior to the selection of a device by the controller of the foot control, the sending of a specific identification code or a data packet from a device is triggered by the user, for example by actuating an actuator of the device or by moving or picking up the device. Moving or picking up the device is detected, for example, by a position sensor or a pressure sensor of the device. The actuator or the sensors preferably generate an actuating signal which is received by a control unit which, in response thereto, is configured to send the specific identification code and, if applicable, the individual rank of the device. Advantageously, this ensures that as soon as a user picks up a previously unused device, an identification code is automatically sent to the foot control unit.

Preferably, the method of wirelessly transmitting data in a medical or dental system further comprises interrupting or terminating an established or existing communication link between the foot control and one of the devices. Thus, the communication link between the foot control and one of the devices is reversible. Preferably, the communication link is interrupted or terminated in a time-dependent manner, for example after expiry of a, in particular predetermined, period of time, preferably after expiry of one second or of several seconds, for example of five or ten seconds. Particularly preferably, the communication link is interrupted or terminated in a time-dependent manner when said period of time has elapsed after the last delivery of wireless operating data or control data for treatment and/or diagnosis to the device that is in communication with the foot control. This advantageously ensures that a currently existing, established communication connection between the foot control and a first device does not hinder the establishment of a new communication connection, in particular between the foot control and another, second device.

Preferably, the foot control is configured to enter a mode with at least reduced transmission power (a standby mode or sleep mode) after expiry of the said period of time or after interruption of the communication link, which mode has at least reduced transmission power compared to an operating mode during communication with the device.

Preferably, the devices controllable by the foot control are arranged to enter a mode with at least reduced transmission power (a standby mode or sleep mode) after expiry of the said period of time or after interruption of the communication link, which mode has at least reduced transmission power compared to an operating mode during communication with the foot control. Preferably, the devices do not transmit an identification code or data packet in the mode with at least reduced transmission power.

After the communication link is broken, it can be re-established between the same or another device and the foot control based on the individual ranks and the controller provided in the foot control, as described above.

Preferably, the specific identification codes and/or data packets sent by the devices, received by the foot control, and stored in the memory element of the foot control are deleted from the memory element of the foot control after a wireless communication link for transmitting operational data to a device is established or when the transmission of operational data is completed. This advantageously enables a new connection to be established to one of the devices.

A computer program product or computer-readable storage medium comprises instructions that, when executed by a computer, cause the computer to perform the method described in the foregoing for wirelessly transmitting data in a medical or dental system that comprises a foot control and a plurality of medical or dental devices for treatment and/or diagnosis. In particular, the computer program product, the computer-readable storage medium, and the computer are parts of, or are at least operatively connected to, the medical or dental system, for example, the foot control and/or the controller.

A foot control for selective wireless control of one of at least two medical or dental devices controllable by the foot control comprises: at least one actuator for setting a value of operating data or control data for treatment and/or diagnosis for the at least two devices, a transmitter and receiver unit for bidirectional wireless communication with the at least two devices including transmission of the operating data settable by the actuator, and a device for data processing with means for carrying out the method described in the foregoing. Preferably, the device for data processing comprises the controller and/or control logic for selecting the device to which the foot control wirelessly transmits operating data or control data for treatment and/or diagnosis.

The foot control or wireless foot control of the medical or dental system comprises, in particular, at least one of the following elements:

a transmitting and receiving unit or a transceiver for transmitting and receiving data and/or electromagnetic energy, in particular for communicating with a transmitting and receiving unit of the devices controllable by the foot control. The transmitting and receiving unit is configured in particular for bidirectional, wireless communication with the at least two devices of the medical or dental system controllable by the foot control. The transmitting and receiving unit is configured, for example, to receive identification codes and/or data packets of the devices and to transmit operating data or control data for treatment and/or diagnosis to the at least two devices. The transmitting and receiving unit comprises, for example, a radio transmitter and/or an antenna and/or electrical conductors which are connected to the controller and which are configured to transmit data and/or electromagnetic energy between the transmitting and receiving unit and the controller;

an energy source for supplying energy to the foot control, in particular to the transmitter and receiver unit and, if necessary, to further components of the foot control requiring electrical energy, in particular to the controller (which can be a microcontroller). The energy source comprises in particular a rechargeable battery that can be charged repeatedly;

at least one user interface, in particular a rotatable or swiveling pedal or actuating element, via which the user generates actuating commands, for example operating data or control data for treatment and/or diagnostics;

the controller (or microcontroller) operatively connected to the user interface and the transmitting and receiving unit. Preferably, the controller comprises control logic configured to process or compare the identification codes or the data packets of the devices and to select that device to which operational data or control data for treatment and/or diagnosis are wirelessly transmitted. Preferably, the data processing device described in the foregoing comprises the controller or microcontroller. Alternatively or additionally, the controller is, for example, configured to receive the user's actuation commands generated via the user interface, preferably to process them and to forward them to the transmitting and receiving unit, so that the transmitting and receiving unit transmits actuation commands, for example operating data or control data, to the devices for treatment and/or diagnosis;

a memory element in which in particular the specific identification codes and/or the data packets assigned to the respective devices are stored or can be stored. The memory element is preferably configured as part of the controller or is operatively connected to the controller, so that in particular data, for example identification codes or data packets, can be transferred between the memory element and the controller.

The foot control is formed as a common foot control for the at least two devices controllable by the foot control. Preferably, each of the devices controllable by the foot control communicates directly with the foot control and vice versa.

Preferably, at least one of the devices or handpieces controllable by the foot control comprises:

a handle portion for holding the device;

a head portion comprising, for example: a tool holder for releasably holding a treatment tool and/or a dispensing device for dispensing a treatment medium and/or a sensor for measuring or determining an operating parameter or a value or condition of a body tissue;

a transmitting and receiving unit or a transceiver for transmitting and receiving data and/or electromagnetic energy, in particular for communicating with the transmitting and receiving unit of the foot control. The transmitting and receiving unit is configured in particular for bidirectional, wireless communication with the foot control of the medical or dental system. For example, the transmitting and receiving unit is configured to transmit the specific identification code or data packet of the device to the foot control and to receive operational data or control data for treatment and/or diagnosis from the foot control. The transmitting and receiving unit comprises, for example, a radio transmitter, an antenna and/or electrical conductors connected to a control unit of the device. The transmitting and receiving unit can be provided either in the handpiece itself or in a supply and/or control unit operatively connected to it, in particular via a line and/or a cable;

an energy source for supplying energy to the device, in particular to the transmitting and receiving unit and, if necessary, to further components of the devices requiring electrical energy, in particular to a microcontroller. The energy source comprises in particular a repeatedly rechargeable accumulator;

an actuating or switching element in order, when actuated by the user, to terminate, for example, a mode with at least reduced transmission power (standby mode or sleep mode) of the device and to put the device into an operating mode with comparatively increased transmission power, in which the device is active and/or is ready to transmit or transmits the identification code or the data packet and/or is ready to receive or receives data of the foot control, in particular the operating data or control data for the treatment and/or diagnosis, and/or is ready to operate. The actuating or switching element comprises, for example, a pushbutton, a pressure sensor or a position sensor.

a control unit for controlling the device, in particular treatment and/or diagnostic modes or values of operating parameters, for example the rotational speed, and/or for receiving sensor data from a sensor of the device mentioned above. Particularly preferably, the control unit is connected to the actuating or switching element and/or to the transmitting and receiving unit, so that the wireless transmission of the identification code or the data packet to the foot control can be controlled by the control unit and/or that operating data or control data for the treatment and/or diagnosis received by the transmitting and receiving unit can be forwarded to the control unit for controlling the device;

a memory element in which the specific identification code assigned to the device or the respective data packet is stored or can be stored. The memory element is preferably configured as part of the control unit or is operatively connected to the control unit, so that in particular data, for example the identification code or the data packet, can be transferred between the memory element, the microcontroller and the transmitting and receiving unit.

Preferably, at least one of the devices controllable by the foot control comprises a medical or dental prophylaxis device, for example a handpiece or device for removing tartar or plaque or discoloration or a handpiece or device for delivering a treatment medium, in particular a powder to a treatment site. Alternatively or additionally, at least one of the devices controllable by the foot control comprises a handpiece or device for processing bone tissue or bone substitute material, for example a saw or a rotating or oscillating drill, or a handpiece or device for treating and/or measuring a body cavity or cavity, for example a root canal or nasal cavity or auditory canal, and/or a handpiece or device for diagnosing, for example, caries or pathological tissue changes.

Preferably, at least one of the devices controllable by the foot control comprises a medical or dental handpiece or is formed by a (wireless) handpiece. Preferably, the handpiece is part of a tabletop device and is operatively connected via a line to a supply and/or control unit.

A medical or dental system comprises a foot control described in the foregoing and a plurality of medical or dental devices for treatment and/or diagnosis, wherein at least two of the plurality of devices are controllable by the foot control and the foot control is configured to selectively (and reversibly) control one of the at least two devices by the foot control. In particular, the plurality of medical or dental devices comprises at least one of the devices described in the foregoing. The medical or dental system is configured in particular as a tabletop device system.

These and other embodiments will be described below with reference to the following drawings.

BRIEF DESCRIPTION OF THE DRAWINGS

FIG. 1 schematically shows a medical or dental system in which data and/or electromagnetic energy are selectively transmitted wirelessly between a foot control and one of a plurality of medical or dental devices.

FIG. 2 schematically shows the memory elements of the medical or dental devices of FIG. 1, each with a specific identification code stored therein.

FIG. 3 schematically shows the storage element of the foot control of FIG. 1 with a plurality of data packets stored therein.

FIG. 4 schematically shows an alternative medical or dental system in which data and/or electromagnetic energy is selectively transmitted wirelessly between a foot control and one of a plurality of medical or dental devices.

FIG. 5 schematically shows the memory elements of the medical or dental devices of FIG. 4, each with a specific data packet stored therein.

DETAILED DESCRIPTION

Figure 6:
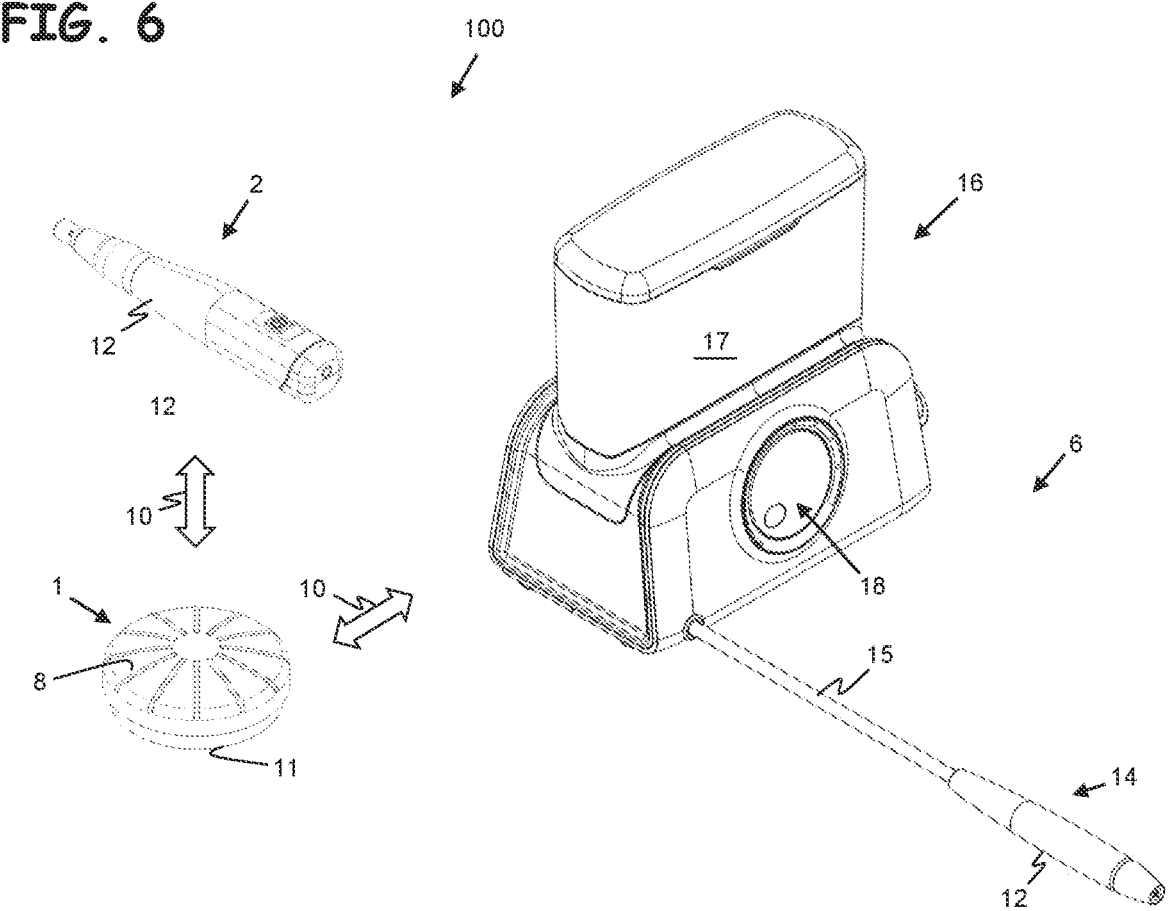
FIG. 6 shows a further medical or dental system in which data and/or electromagnetic energy are selectively transmitted wirelessly between a foot control and one of a plurality of medical or dental devices.

The medical or dental systems 50, 70, 100 shown in FIGS. 1, 4 and 6 each comprise a foot control 1 and a plurality of medical or dental devices 2, 2A-2N; 6, 6A-6N for treatment and/or diagnosis. The devices 2, 2A-2N; 6, 6A-6N and the foot control 1 are configured such that data and/or electromagnetic energy is wirelessly transmittable between the foot control 1 and the devices 2, 2A-2N; 6, 6A-6N by radio communication (this is symbolized by the arrow 10). Each of the devices 2, 2A-2N; 6, 6A-6N is selectively controllable wirelessly by the foot control 1, for example with control data for the operation of the respective device 2, 2A-2N; 6, 6A-6N, in particular with control data for treatment and/or diagnosis. For bidirectional communication and transmission of data and/or electromagnetic energy, the foot control 1 and each of the devices 2, 2A-2N; 6, 6A-6N comprise a transmitting and receiving unit 9, 9A for transmitting and receiving data and/or electromagnetic energy.

The foot control unit 1 comprises, among other things, a base plate 11, at least one actuating element 8 which can be rotated or pivoted relative to the base plate 11 in particular and via which the user generates actuating commands, for example operating data or control data for treatment and/or diagnosis, and a controller or microcontroller or computer 7. The microcontroller 7 forms the central control unit of the foot control 1 and is connected to the actuating element 8 and the transmitting and receiving unit 9, for example to receive and/or process and/or forward actuating commands of the actuating element 8 and/or control data for treatment and/or diagnosis and/or data received from the devices 2, 2A-2N; 6, 6A-6N, for example a specific identification code or a data packet of one of the devices 2A-2N; 6A-6N.

The foot control 1 further comprises control logic such as in a controller 3 (or microcontroller), which is configured to select, on the basis of specific data packets 4A-4N; 5A-5N, each assigned to one of the devices 2, 2A-2N; 6, 6A-6N, one of the devices 2, 2A-2N; 6, 6A-6N controllable by the foot control 1, to which operating data or control data for treatment and/or diagnosis are wirelessly transmitted. In particular, the controller 3 can be formed as part of the computer 7 or other device.

Figure 7:
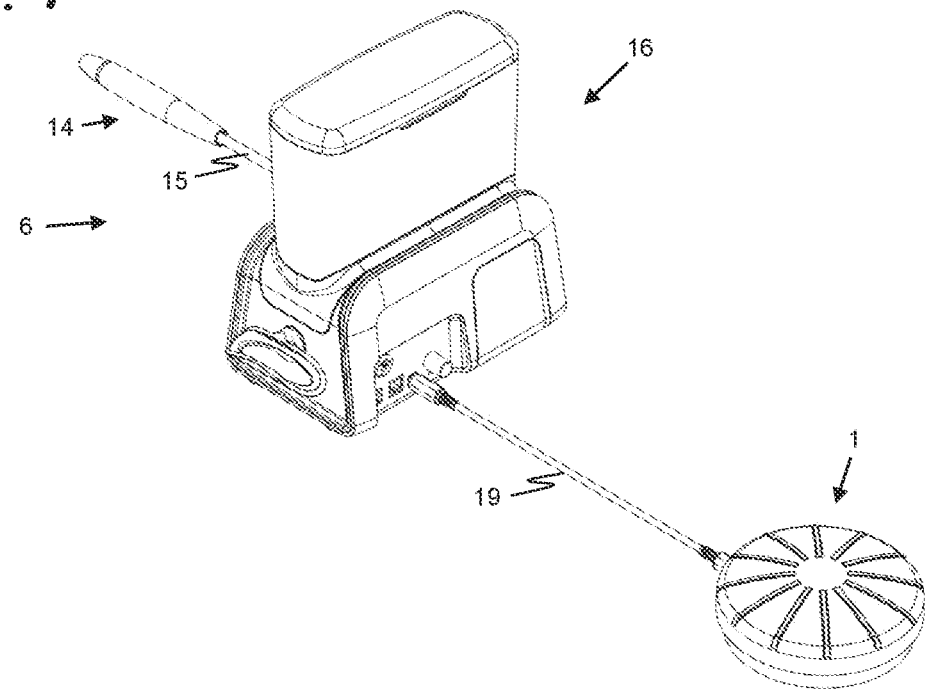
FIG. 7 shows the foot control and one of the multiple medical or dental devices of FIG. 6 during pairing.

The devices 2A-2N; 6A-6N shown only schematically in FIGS. 1 and 4 and the devices 2, 6 of FIGS. 6, 7 have an outer sleeve 12, which in particular also serve to hold the devices 2, 2A-2N; 6, 6A-6N with a hand. Each device 2, 2A-2N; 6, 6A-6N comprises a transmitter and receiver unit 9A for wireless communication 10 with the foot control 1, in particular for wireless transmission of data and/or electromagnetic energy between the device 2, 2A-2N; 6, 6A-6N and the foot control 1, and a memory element 13. The memory element 13 and the transmitting and receiving unit 9A of each device 2, 2A-2N; 6, 6A-6N are communicatively connected so that data stored in the memory element 13 is transmitted to and from the transmitting and receiving unit 9A, and optionally data is received from the transmitting and receiving unit 9A and forwarded to the memory element 13 for storage.

Various components may be provided inside or on the outer sleeve 12, depending on the type and intended use of the devices 2, 2A-2N; 6, 6A-6N, such as coupling elements, media lines, media delivery devices or openings, radiation sources, radiation conductors, sensors, electrical lines, tool holding devices, drive elements, actuating elements, display devices, a control unit for controlling the device, etc.

In the following, the embodiment according to FIGS. 1-3 is further explained. FIG. 2 schematically shows the memory elements 13 of the devices 2A-2N (the order corresponding to devices 2A-2N), wherein a specific identification code is stored in each of the memory elements 13. As an example, the identification code is indicated as "WHTW" for the first device 2A, "WHUL" for the second device 2B, "WHST" for the third device 2C, and "WHNN" for the fourth device 2N. Each specific identification code is associated with a specific device 2A-2N, namely that device 2A-2N in whose memory element 13 it is stored. Each specific identification code is unique and distinguishable from any other identification code. Thus, each device 2A-2N can be uniquely identified based on the or its specific identification code.

FIG. 3 shows four data packets 4, 4A-4N, which are stored in the actuator 8, in particular in a memory element of the microcontroller or computer 7, according to the embodiment of FIGS. 1-3. Each of the data packets 4A-4N comprises one of the specific identification codes (WHTW, WHUL, WHST, WHNN) of the devices 2A-2N controllable by the foot control 1 and an individual, unique rank of a ranking of the devices 2A-2N controllable by the foot control 1 associated with each device 2A-2N. The ranks or the values of the ranks are exemplarily configurated as "0", "2", "4" and "6", wherein the rank "0" is assigned to the device 2A with the identification code "WHTW", the rank "2" is assigned to the device 2B with the identification code "WHUL", the rank "4" is assigned to the device 2C with the identification code "WHST" and the rank "6" is assigned to the device 2N with the identification code "WHNN". Thus, (via the identification code) each of the devices 2A-2N controllable by the foot control 1 is assigned its own specific data packet 4 and thereby an individual, unique rank.

According to the embodiment of FIGS. 1-3, the selection to which of the devices 2A-2N controllable by the foot control 1 operating data or control data are wirelessly transmitted is done as follows: in order for operating data to be transmitted to a device 2A-2N, the device 2A-2N must be active or in an operating mode in which it is ready, in particular, for wireless transmission and reception of data. Activating the device 2A-2N or putting it into the operating mode can, for example, be performed by the user grasping the device 2A-2N, moving it and/or actuating an actuating element. In the following, an active device 2A-2N transmits its respective, specific identification code wirelessly to the foot control 1 via the transmitting and receiving unit 9A.

If a plurality of devices 2A-2N are active, or if (within a predetermined period of time) a plurality of devices 2A-2N transmit their respective specific identification codes, the foot control 1 receives these specific identification codes and forwards them to the controller 3. Based on the received identification codes, the controller 3 recognizes which devices 2A-2N are active. By comparing the identification codes of the devices 2A-2N stored in the data packets 4 with the received identification codes of the active devices 2A-2N, the controller further determines which individual rank each active devices 2A-2N has. Depending on which individual rank of the active devices 2A-2N is prioritized, the controller or foot control 1 selects that device 2A-2N for the exclusive wireless transmission of operating data, in particular control data for treatment and/or diagnosis, from which the foot control 1 has received an identification code and which has a prioritized individual rank or value in the ranking compared to the other active devices 2A-2N from which the foot control 1 has received an identification code.

For example, if the devices 2A, 2B send their specific identification codes "WHTW" and "WHUL" and that device whose rank or value is lower in the ranking is prioritized, the controller or foot control 1 selects the device 2A with the identification code "WHTW" and rank "0" for wireless transmission of operational data.

In the following, the embodiment according to FIGS. 4-5 will be further explained. FIG. 5 schematically shows the memory elements 13 of the devices 6A-6N (the order corresponding to devices 6A-6N), wherein a specific data packet 5, 5A-5N is stored in each of the memory elements 13. Each of the data packets 5A-5N comprises a specific identification code (WHTW, WHUL, WHST, WHNN) of the devices 6A-6N controllable by the foot control 1 and an individual unique rank of a ranking of the devices 6A-6N controllable by the foot control 1 assigned to each device 6A-6N. The ranks or the values of the ranks are exemplarily configurated as "A0", "B0", "C0" and "D0", wherein the rank "A0" is assigned to the device 6A with the identification code "WHTW", the rank "B0" is assigned to the device 6B with the identification code "WHUL", the rank "C0" is assigned to the device 6C with the identification code "WHST" and the rank "D0" is assigned to the device 6N with the identification code "WHNN". Thus, each of the devices 2A-2N controllable by the foot control 1 is assigned its own specific data packet 4 with a specific identification code, which is in particular unique and distinguishable from any identification code of the other devices 2A-2N, and an individual unique rank.

According to the embodiment of FIGS. 4-5, the selection to which of the devices 6A-6N controllable by the foot control 1 operating data or control data are wirelessly transmitted is done as follows: in order for operating data to be transmitted to a device 6A-6N, the device 6A-6N must be active or in an operating mode in which it is ready, in particular, for wireless transmission and reception of data. Activating the device 6A-6N or putting it into the operating mode can, for example, be performed by the user grasping the device 6A-6N, moving it and/or actuating an actuator. In the following, an active device 6A-6N sends its respective, specific data packet 5 wirelessly to the foot control 1 via the transmitter and receiver unit 9A.

If a plurality of devices 6A-6N are active or if a plurality of devices 6A-6N send (within a predetermined period of time) their respective specific data packet 5, the foot control 1 receives these specific data packets 5 and forwards them to the controller 3. Based on the identification codes contained in the received data packets 5, the controller 3 recognizes which devices 6A-6N are active and can determine their individual ranks or the values of the ranks. Depending on which individual rank of the active devices 6A-6N is prioritized, the controller or foot control 1 selects that device 6A-6N for the exclusive wireless transmission of operational data, in particular control data for treatment and/or diagnosis, from which the foot control 1 has received a data packet 5 and which has an individual rank or value prioritized in the ranking compared to the other active devices 6A-6N from which the foot control 1 has received a data packet 5.

For example, if the devices 6B and 6C send their specific data packets 5B (with the identification code "WHUL" and the rank "B0") and 5C (with the identification code "WHST" and the rank "C0") and if that device is prioritized whose rank has the letter preceding in the alphabet, the controller or foot control 1 selects the device 6B with the identification code "WHUL" and the rank "B0" for wireless transmission of operational data.

For both embodiments according to FIGS. 1-3 and 4-5, if only one of the devices 2A-2N, 6A-6N is active or transmits (within a predetermined time period) an identification code, the foot control selects this device 2A-2N, 6A-6N and transmits exclusively to this device 2A-2N, 6A-6N operational data or control data for treatment and/or diagnosis. Preferably, the controller here is configured such that the determination of the individual rank of the only active device 2A-2N, 6A-6N or the comparison of individual ranks is not performed or is skipped.

The medical or dental system 100 shown in FIG. 6 is configured as a prophylaxis table top device. The system 100 comprises a foot control 1, which corresponds to the foot controls of FIGS. 1-5. The system 100 further comprises a device or handpiece 2 for rotatingly driving a tool, for example a prophy cap or a brush, and a device 6 with an oscillating drive, in particular an ultrasonic drive, for oscillatingly driving a tool. Both devices 2, 6 are configured to communicate wirelessly (see arrows 10) with the foot control 1 and in particular to receive operating data or control data from the foot control 1 for the treatment.

The unit 6 comprises a handpiece 14, in particular a scaler handpiece for removing calculus, which is connected to a supply and/or control unit 16 via a cable 15. Preferably, the transmitter and receiver unit 9A of the device 6 is provided in the supply and/or control unit 16. The supply and/or control unit 16 comprises a controller for controlling the operation of the handpiece 14, an actuator 18 for setting or selecting operating parameters or modes, and at least one container 17 for a treatment medium. The treatment medium and control signals are supplied to the handpiece 14 via the cable 15.

The selection to which of the devices 2, 6 controllable by the foot control 1 operating data or control data are wirelessly transmitted can be implemented in the medical or dental system 100 according to the embodiment of FIGS. 1-3 or FIGS. 4-5. Accordingly, the data packets 4, 5 are provided either in the foot control 1 or in the devices 2, 6, and the system 100 is operated either according to the method described in the foregoing of FIGS. 1-3 or FIGS. 4-5.

In the medical or dental system 100, it is further provided that the individual ranks of the devices 2, 6 in the data packets 4 or 5 are determined through pairing the foot control 1 with the devices 2, 6. According to the system 100, the device 2 is paired wirelessly with the foot control 1, while the device 6 is paired with the foot control 1 via a cable 19 (see FIG. 7). For pairing with or without cable, different drivers are required, which are preferably stored in the foot control 1. The control units of the devices 2, 6 and/or the controller or the microcontroller 7 of the foot control 1 are configured to recognize the different drivers and, preferably on the basis of the different drivers, the type of pairing and to assign to the device 2, 6, which is currently being paired with the foot control, a rank corresponding to the driver and/or the type of pairing. In particular, the control units of the devices 2, 6 and/or the controller or the microcontroller 7 of the foot control 1 are configured to assign the rank to the identification code of the device 2, 6 that is currently being paired with the foot control in order to form the data packets 4, 5, or to paste the rank in the data packet 4, 5 of the respective device 2, 6.

The embodiments described or illustrated serve in particular to illustrate the invention. The features disclosed in one embodiment are therefore not limited to this embodiment but can be combined individually or together with one or more features of one of the other embodiments.

What is claimed is:

1. A method for wireless transmission of data in a medical or dental system having
    a foot control having a controller, and
    a plurality of medical or dental devices for treatment and/or diagnosis, wherein at least a first device and a second device of the plurality of medical or dental devices are selectively wirelessly controllable by the foot control, wherein
    the first device and the second device each comprises a specific device identification code, wherein
    the first device and the second device each is assigned a data packet comprising the specific device identification code and an individual rank of a ranking of the devices controllable by the foot control, wherein the data packets of the first device and the second device are provided in the foot control,
    the method comprising:
    wirelessly receiving the specific device identification code with the foot control from at least one of the first device and the second device, and
    recognizing with the foot control, on the basis of the received device identification code(s) and on the basis of the data packets stored in the foot control, if any of the at least first device and second device is an active device and the individual rank of each active device, and wherein each individual rank of the first device and the second device is unique and stored in one of the foot control or the respective first and second device prior to initial control by the foot control.

2. The method for wireless transmission of data according to claim 1, further comprising determining if there is more than one active device, then selecting the active device for wireless transmission of operating data which has a prioritized individual rank in the ranking compared to other active devices.

3. The method for wireless transmission of data according to claim 1, further comprising determining that there is only one active device, then selecting the active device for wireless transmission of operational data.

4. A method for wireless transmission of data in a medical or dental system having
    a foot control having a controller, and
    a plurality of medical or dental devices for treatment and/or diagnosis, wherein at least a first device and a second device of the plurality of medical or dental devices are selectively wirelessly controllable by the foot control, wherein
    the first device and the second device each comprises a data packet comprising a specific device identification code and an individual rank of a ranking of the devices controllable by the foot control, the method comprising:
    wirelessly receiving data packets with the foot control from at least one of the first device and the second device, and
    recognizing with the foot control, on the basis of the received data packets, if any of the first device and the second device is an active device and the individual rank of each active device, and wherein each individual rank of the first device and the second device is unique and stored in one of the foot control or the respective first and second device prior to initial control by the foot control.

5. The method for wireless transmission of data according to claim 4, further comprising determining if there is more than one active device, then selecting the active device for wireless transmission of operating data which has a prioritized individual rank in the ranking compared to other active devices.

6. The method for wireless transmission of data according to claim 4, further comprising determining that there is only one active device, then selecting the active device for wireless transmission of operational data.

7. The method for wireless transmission of data according to claim 1, further comprising
    determining the individual ranks of the data packets by pairing and/or during pairing of the first device and the second device with the foot control.

8. The method for wireless transmission of data according to claim 7, further comprising determining
    the individual ranks by the order in which the devices controllable by the foot control are paired with the foot control.

9. The method for wireless transmission of data according to claim 7, further comprising determining
    the individual ranks based on the driver used for pairing and/or the type of pairing between the foot control and the devices controllable by the foot control.

10. The method for wireless transmission of data according to claim 4, further comprising determining
    the individual ranks of the data packets by pairing and/or during pairing of the devices controllable by the foot control with the foot control.

11. The method for wireless transmission of data according to claim 10, further comprising determining the individual ranks by the order in which the devices controllable by the foot control are paired with the foot control.

12. The method for wireless transmission of data according to claim 10, further comprising determining the individual ranks based on the driver used for pairing and/or the type of pairing between the foot control and the devices controllable by the foot control.

13. A non-transitory computer-readable storage medium comprising instructions that, when executed by a computer, cause the computer to perform the method of claim 1.

14. A non-transitory computer-readable storage medium comprising instructions that, when executed by a computer, cause the computer to perform the method of claim 4.

15. A foot control for selective wireless control of medical or dental devices, comprising: a controller programmed to wirelessly receive specific identification codes from at least a first device and a second device of a plurality of the medical or dental devices controllable by the foot control and to access data packets stored in the foot control comprising the identification codes for the first device and the second device and individual ranks for the first device and the second device, and to recognize if any of the first device and the second device is an active device and the individual rank of each active device; at least one actuator for setting a value of operating data for at least the first device and the second device; and a transmitting and receiving unit for bidirectional wireless communication with at least the first device and the second device including transmission of the operating data settable by the actuator, wherein each individual rank of the first device and the second device is unique and stored in one of the foot control or the respective first and second device prior to initial control by the foot control.

16. The foot control according to claim 15, wherein if there is more than one active device, then the controller is programmed to select the active device for wireless transmission of operating data which has a prioritized individual rank in a ranking compared to other active devices.

17. A foot control for selective wireless control of medical or dental devices, comprising: a controller programmed to wirelessly receive data packets from at least a first device and a second device of a plurality of the medical or dental devices controllable by the foot control, the data packets comprising identification codes for the first device and the second device and individual ranks for the first device and the second device, and to recognize if any of the first device and the second device is an active device and the individual rank of each active device; at least one actuator for setting a value of operating data for at least the first device and the second device; and a transmitting and receiving unit for bidirectional wireless communication with at least the first device and the second device including transmission of the operating data settable by the actuator, wherein each individual rank of the first device and the second device is unique and stored in one of the foot control or the respective first and second device prior to initial control by the foot control.

18. The foot control of claim 17, wherein if there is more than one active device, then the controller is programmed to select the active device for wireless transmission of operating data which has a prioritized individual rank in a ranking compared to other active devices.

19. A medical or dental system, comprising a foot control according to claim 15 and a plurality of medical or dental devices for treatment and/or diagnosis that includes at least the first device and the second device.

20. A medical or dental system, comprising a foot control according to claim 17 and a plurality of medical or dental devices for treatment and/or diagnosis that includes at least the first device and the second device.

* * * * *